(12) United States Patent
Justis

(10) Patent No.: US 8,002,806 B2
(45) Date of Patent: Aug. 23, 2011

(54) BOTTOM LOADING MULTI-AXIAL SCREW ASSEMBLY

(75) Inventor: Jeff R. Justis, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1465 days.

(21) Appl. No.: 11/254,874

(22) Filed: Oct. 20, 2005

(65) Prior Publication Data

US 2007/0090238 A1    Apr. 26, 2007

(51) Int. Cl.
*A61B 17/70* (2006.01)
(52) U.S. Cl. ........ 606/264; 606/246; 606/265; 606/267; 606/269; 606/272; 606/266
(58) Field of Classification Search .................. 606/253, 606/266–270, 272
See application file for complete search history.

(56) References Cited

U.S. PATENT DOCUMENTS

| | | | |
|---|---|---|---|
| 4,946,458 A | 8/1990 | Harms et al. | |
| 5,190,543 A | 3/1993 | Schlapfer | |
| 5,501,684 A | 3/1996 | Schlapfer et al. | |
| 5,520,689 A | 5/1996 | Schlapfer et al. | |
| 5,536,268 A | 7/1996 | Griss | |
| 5,549,608 A | 8/1996 | Errico et al. | |
| 5,562,661 A | 10/1996 | Yoshimi et al. | |
| 5,575,792 A | 11/1996 | Errico et al. | |
| 5,586,984 A | 12/1996 | Errico et al. | |
| 5,647,873 A | 7/1997 | Errico et al. | |
| 5,672,176 A | 9/1997 | Biedermann et al. | |
| 5,690,630 A | 11/1997 | Errico et al. | |
| 5,728,098 A | 3/1998 | Sherman et al. | |
| 5,733,285 A | 3/1998 | Errico et al. | |
| 5,797,911 A | 8/1998 | Sherman et al. | |
| 5,817,094 A | 10/1998 | Errico et al. | |
| 5,882,350 A | 3/1999 | Ralph et al. | |
| 5,885,286 A | 3/1999 | Sherman et al. | |
| 5,891,145 A | 4/1999 | Morrison et al. | |
| 5,989,254 A * | 11/1999 | Katz .............................. | 606/308 |
| 6,063,090 A * | 5/2000 | Schlapfer ..................... | 606/270 |
| 6,074,391 A | 6/2000 | Metz-Stavenhagen et al. | |
| 6,132,432 A | 10/2000 | Richelsoph | |
| 6,187,005 B1 * | 2/2001 | Brace et al. .................... | 606/264 |
| 6,248,105 B1 * | 6/2001 | Schlapfer et al. ............. | 606/266 |
| 6,280,442 B1 | 8/2001 | Barker et al. | |
| 6,331,179 B1 * | 12/2001 | Freid et al. .................... | 606/279 |
| 6,368,321 B1 | 4/2002 | Jackson | |
| 6,402,752 B2 | 6/2002 | Schaffler-Wachter et al. | |
| 6,520,963 B1 | 2/2003 | McKinley | |
| 6,537,276 B2 | 3/2003 | Metz-Stavenhagen | |
| 6,660,004 B2 | 12/2003 | Barker et al. | |
| 6,692,500 B2 | 2/2004 | Reed | |

(Continued)

FOREIGN PATENT DOCUMENTS

DE    4107480    9/1992

(Continued)

*Primary Examiner* — Thomas C Barrett
*Assistant Examiner* — Michael T Schaper

(57) ABSTRACT

Anchor assemblies are provided to secure one or more implants along the spinal column that include a retainer in a receiver member. The retainer is configured to distribute the forces exerted on the retainer toward the proximal end of the retainer where it may deform without deforming, distorting or altering the retainer where it supports the anchor member in the receiver member. The desired positioning of the anchor member relative to the retainer and receiver member can thus be attained even when the retainer is subject to deformation forces.

20 Claims, 3 Drawing Sheets

U.S. PATENT DOCUMENTS

| | | | |
|---|---|---|---|
| 6,716,214 B1 * | 4/2004 | Jackson | 606/266 |
| 6,736,820 B2 | 5/2004 | Biedermann et al. | |
| 6,800,078 B2 | 10/2004 | Reed | |
| 6,837,889 B2 | 1/2005 | Shluzas | |
| 7,559,943 B2 | 7/2009 | Mujwid | |
| 7,850,718 B2 * | 12/2010 | Bette et al. | 606/267 |
| 2002/0026193 A1 | 2/2002 | Barker et al. | |
| 2004/0039384 A1 * | 2/2004 | Boehm et al. | 606/61 |
| 2004/0097933 A1 | 5/2004 | Lourdel et al. | |
| 2004/0116929 A1 | 6/2004 | Barker et al. | |
| 2004/0127897 A1 * | 7/2004 | Freid et al. | 606/61 |
| 2004/0172022 A1 | 9/2004 | Landry et al. | |
| 2004/0236330 A1 | 11/2004 | Purcell et al. | |
| 2005/0154391 A1 * | 7/2005 | Doherty et al. | 606/61 |
| 2005/0159750 A1 | 7/2005 | Doherty | |
| 2005/0177154 A1 | 8/2005 | Moumene et al. | |
| 2005/0187548 A1 | 8/2005 | Butler et al. | |
| 2005/0261687 A1 | 11/2005 | Garamszegi et al. | |
| 2006/0089644 A1 * | 4/2006 | Felix | 606/61 |
| 2007/0043355 A1 | 2/2007 | Bette et al. | |
| 2007/0088357 A1 | 4/2007 | Johnson et al. | |
| 2008/0195159 A1 | 8/2008 | Kloss et al. | |
| 2008/0306546 A1 | 12/2008 | Zucherman et al. | |

FOREIGN PATENT DOCUMENTS

| | | |
|---|---|---|
| DE | 4243951 | 7/1994 |
| DE | 19605640 | 8/1997 |
| EP | 0626828 | 12/1994 |
| WO | WO 98/25534 | 6/1998 |
| WO | WO 2005/018471 | 3/2005 |
| WO | WO 2009/106733 | 9/2009 |

* cited by examiner

BOTTOM LOADING MULTI-AXIAL SCREW ASSEMBLY

BACKGROUND

Spinal implants can be engaged to or along one or more vertebrae of the spinal column for the treatment of various spinal conditions. Fasteners can be provided to secure the implant to a particular location along the spinal column. The implants can be provided to stabilize the spinal column for treatment, either by fixing the spinal column or by permitting at least some motion of the stabilized motion segments.

Multi-axial and uni-axial screws have been employed for securing elongated implants, such as rods or plates, along one or more motion segments of the spinal column. Such fasteners can comprise many components or parts that make placement and manipulation of the fastener and the elongated implant cumbersome during surgery to achieve the desired position relative to the spinal anatomy. Furthermore, manipulation of the fasteners can result in deformation of components thereof that make achieving the desired fit between the fastener components and/or the implant difficult to achieve.

SUMMARY

According to one aspect, a system for stabilizing a bony segment includes an elongated implant and an anchor assembly engageable to the elongated implant to secure it to the spinal column. The anchor assembly includes a receiver member, an anchor member, a seat member and a retainer. The receiver member defines a passage for receiving the implant and a distal opening extending transversely to the passage through which a bone engaging portion of the anchor member extends. A seat member is positioned between the implant and the head of the anchor member in the receiver member. A retainer includes a distal seat end supported on the lip in the receiver member and a central receptacle. The retainer extends proximally from the distal seat end and about the head of the anchor member to a proximal end. The seat member is received in the receptacle in contact with the head.

In another aspect, an anchoring assembly for securing an elongated implant along a spinal column includes a receiver member, an anchor member and a retainer. The receiver member defines a passage for receiving the implant and a distal opening extending transversely to the passage through which a bone engaging portion of the anchor member extends. The retainer includes a body defining a receptacle pivotally capturing the head of the anchor member therein and in the receiver member. The body includes a proximal opening adjacent a proximal end of the head and a lip about a distal opening of the retainer in contact with a distal side of the head. The retainer further includes a cutout in the body extending through the lip and in communication with the receptacle. The cutout provides a location at the distal opening of the retainer to receive the anchor member in a pivotal orientation relative to the retainer and the receiver member. The cutout provides a greater pivot angle than is attainable at locations about the distal opening of the retainer not occupied by the cutout.

According to another aspect, an anchor assembly for securing an elongated implant along the spinal column includes a receiver member, an anchor member, and a retainer in the receiver member. The receiver member defines a passage for receiving the implant and a distal opening extending transversely to passage through which a bone engaging portion of the anchor member extends. The retainer includes a body defining a receptacle pivotally capturing the head of the anchor member therein. The body includes a proximal end and extends along the head to a distal seat end positionable in contact with the receiver member. The retainer includes a number of axial passages in the body extending from the distal seat end to a location distal of the proximal end of the retainer. The number of passages divides the body into a plurality of wall segments moveable relative to one another about the proximal end of the retainer body.

In yet another aspect, an anchor assembly for securing an elongated implant along the spinal column includes a receiver member, an anchor member, and a retainer in the receiver member. The receiver member defines a passage for receiving the implant and a distal opening extending transversely to the passage through which a bone engaging portion of the anchor member extends. The retainer includes a body defining a receptacle pivotally capturing the head of the anchor member therein. The body includes a proximal end and extends along the head to a distal seat end positionable in contact with the receiver member. The retainer includes a plurality of wall segments resiliently movable relative to one another about a hinge portion adjacent the proximal end of the retainer to contract the body to receive the body through the distal opening of the receiver member and to return the body after contracting the body to engage the distal seat end with the receiver member.

These and other aspects will be discussed further below.

DETAILED DESCRIPTION OF THE ILLUSTRATED EMBODIMENTS

Figure 1:
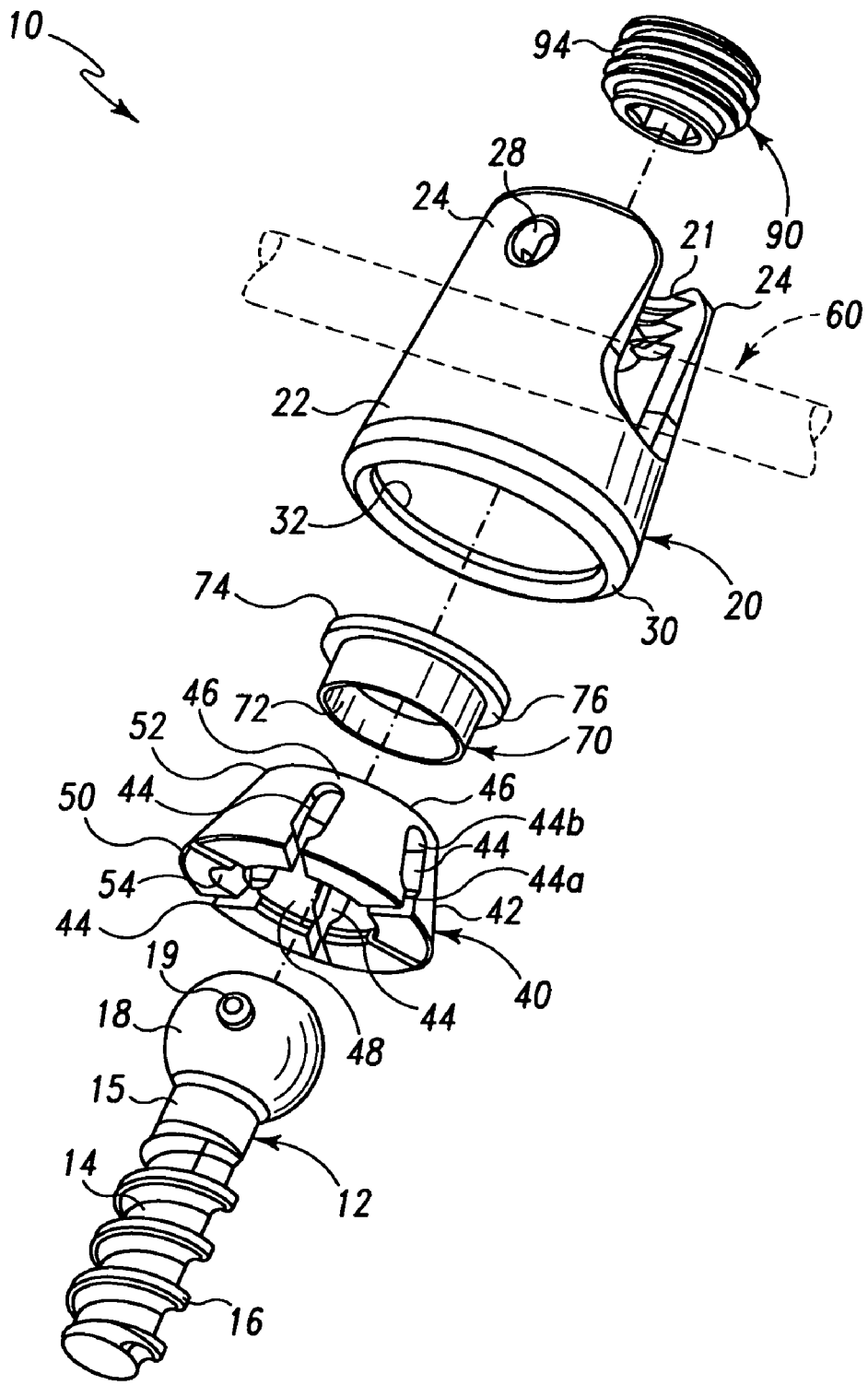
FIG. 1 is an exploded view of an anchor assembly.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Anchor assemblies are provided to secure one or more implants along the spinal column that include a retainer in a receiver member. The retainer is configured to distribute the forces exerted on the retainer toward the proximal end of the retainer where it may deform without deforming, distorting or altering the retainer where it supports the anchor member in the receiver member. The desired positioning of the anchor member relative to the retainer and receiver member can thus be attained even when the retainer is subject to deformation forces.

Anchor assemblies are further provided for securing implants along the spinal column that include a retainer positioned about a head of an anchor member in a receiver member. The anchor assembly can include a seat member positioned through a proximal end opening of the retainer in contact with the head of the anchor member.

Anchor assemblies are also provided for securing implants along the spinal column that include a retainer positioned about a head of an anchor member in a receiver. The retainer can include at least one elongated passage extending axially from a distal end thereof to a living hinge portion adjacent a proximal end of the retainer. The at least one passage divides the body of the retainer into wall segments that are moveable relative to one another to accommodate insertion of the anchor member into the retainer and then retain the anchor member therein. The wall segments are also moveable to accommodate insertion of the retainer into the receiver member, and then return toward a pre-insertion configuration to contact the receiver member and maintain the retainer in the receiver member.

Anchor assemblies are also provided for securing implants along the spinal column that include a retainer positioned about a head of an anchor member in a receiver member. The retainer can include elongated passages extending axially from a distal end thereof and the anchor member can include at least one pin extending from the head thereof that is received in a corresponding one of the at least one passages.

Anchor assemblies are further provided for securing implants along the spinal column that include a retainer including an elongated frusto-conical configuration positioned about a head of an anchor member in a receiver. The retainer can include a distal end with a seat configured to contact the receiver member and support the head of the anchor member in the receiver and a cutout interrupting the seat to provide a location where the anchor member can be received in an angular orientation relative to an axis of the receiver member that is greater than an angular orientation attainable at locations about the seat not occupied by the cutout.

Referring now to FIG. 1, there is shown an anchor assembly 10 in an exploded view including an anchor member 12, a receiver member 20, a retainer 40, and a seat member 70. Retainer 40 is positionable about a head of anchor member 12 in receiver member 20. An implant 60 is positionable on, in or about receiver member 20, and engaging member 90 is movable relative to implant 60 and engageable in receiver member 20 to secure implant 60 to anchor assembly 10. Anchor assembly 10 includes seat member 70 between anchor member 12 and implant 60. Seat member 70 includes a proximally oriented implant support surface 74 for contacting implant 60 when engaged in anchor assembly 10. Implant 60 can be engaged along one or more vertebrae of the spinal column with one or more anchor assemblies 10 or any other type of fastener in combination with one or more anchor assemblies 10 to provide, for example, a spinal stabilization system.

Receiver member 20 includes a lower portion 22 that can be in the form of a bowl, cylinder or other suitable configuration to form a receptacle to receive retainer 40 with head 18 of anchor member 12 therein. Opposite arms 24 extend axially and proximally from opposite sides of lower portion 22. Opposing arms 24 define an implant receiving passage 21 therebetween that is sized to receive implant 60 proximally of seat member 70. Implant receiving passage 21 provides a saddle-type arrangement to receive implant 60 and engaging member 90. Arms 24 can each include an internal thread profile to threadingly receive engaging member 90, although other engagement structures to secure engaging member 90 and receiver member 20 to one another are contemplated.

Arms 24 also each include an outer recess 28 to receive and facilitate engagement by and manipulation with insertion and/or reduction instrumentation (not shown.)

Anchor member 12 in the illustrated embodiment is a bone screw and includes a shaft 14 having a thread profile 16 therealong and enlarged head 18 at a proximal end of anchor member 12. Head 18 includes a proximally opening tool recess (not shown) to receive a driving tool to facilitate engagement of anchor member 12 to the underlying bone. A pair of opposite pins 19 (only one shown in FIG. 1) extend outwardly from the sides of head 18. Pins 19 provide an engagement structure to secure and maintain retainer 40 in a desired relative positioning to head 18. Other engagement structures are also contemplated. For example, the sides of head 18 can be flat to engage opposite flat surfaces in retainer 40. Various forms for anchor member 12 are contemplated, including threaded and non-threaded anchors, uni-planar and multi-axial pivoting arrangements. Bone engaging portions in the form of hooks, clamps, spikes, cables, interbody implants, fusion devices, non-cannulated screws, fenestrated screws, and bolts, are also contemplated, for example.

Receiver member 20 can be sized to receive seat member 70 adjacent to and proximally of head 18 of anchor member 12. Seat member 70 includes a central opening 72 that is in communication with head 18 of anchor member 12 to receive a driving tool (not shown) to apply a driving force to anchor member 12. Seat member 70 includes a proximally oriented implant support surface 74 defined about a flange 76 extending about central opening 72. Flange 76 can engage receiver member 20 to axially retain seat member 70 therein. Flange 76 can be integral with seat member 70, as shown, or can be a separate component.

Engaging member 90 is engageable with receiver member 20 to secure implant 60 in engagement with seat member 70. Engaging member 90 can include a proximal break-off portion (not shown) and a receiver engaging portion 94, although embodiments without a break-off portion are contemplated as shown. Receiver engaging portion 94 is illustrated as an externally threaded set screw that engages the internal thread profile along arms 24. Other configurations are also contemplated for engaging member 90, including internally threaded nuts and multiple component engaging members including internally and/or externally threaded portions. Engaging members are also contemplated that do not threadingly engage receiver member 20, and engaging relationships that include friction fits, adhesives, fusions, snap fits, and bayonet-locks are contemplated.

Retainer 40 includes a cylindrical body 42 extending between a distal seat end 50 and a proximal end 52. Body 42 defines a receptacle 48 for pivotally receiving head 18 of anchor member 12. Body 42 can include a generally frusto-conical shape defined by its outer wall surface that tapers proximally. The inner shape of body 42 can be any shape suitable for pivotally retaining head 18 of anchor member 12 therein.

Figure 6:
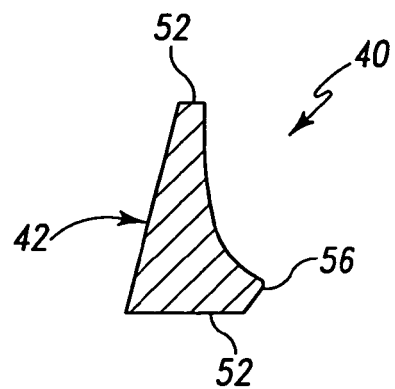
FIG. 6 is a section view of a portion the retainer showing a wall profile.

Body 42 includes a number of axially extending passages 44 extending therealong from distal seat end 50 to a proximal hinge portion 46. Each of the passages 44 includes a narrowed distal portion 44a and a proximal receiving portion 44b. As shown in FIG. 6, the wall of body 42 can reduce in thickness from distal seat end 50 to proximal end 52. The reduced wall thickness adjacent proximal end 52 forms living hinge portions 46 in body 42 adjacent the proximal ends of the respective passages 44. The adjacent wall segments formed by the respective passages 44 are moveable about hinge portions 46 to expand or contract receptacle 48 in body 42.

A lip 56 about distal seat portion 50 is configured to normally contact the underside of head 18 of anchor member 12 and retain head 18 in receptacle 48. Head 18 of anchor member 12 is inserted into receptacle 48 of retainer 40 through the distal opening defined by distal seat end 50. Pins 19 are aligned with respective ones of the passages 44, and can pass through the aligned ones of the narrowed distal portions 44a by flexing body 42 outwardly to increase the space between the narrowed distal portions 44a. When pins 19 are received in the proximal slot portions 44b, body 42 can return toward its pre-flexed condition, and the narrowed distal portions 44a retain pins 19 in the proximal portions 44b, coupling anchor member 12 to retainer 40. Lip 56 can move outwardly as the respective wall segments including lip 56 are moved outwardly to accommodate insertion of head 18 of anchor member 12 thereby. When head 18 is received into receptacle 48, return of the wall segments toward their pre-insertion position engages lip 56 to the distal side of head 18.

Figure 2:
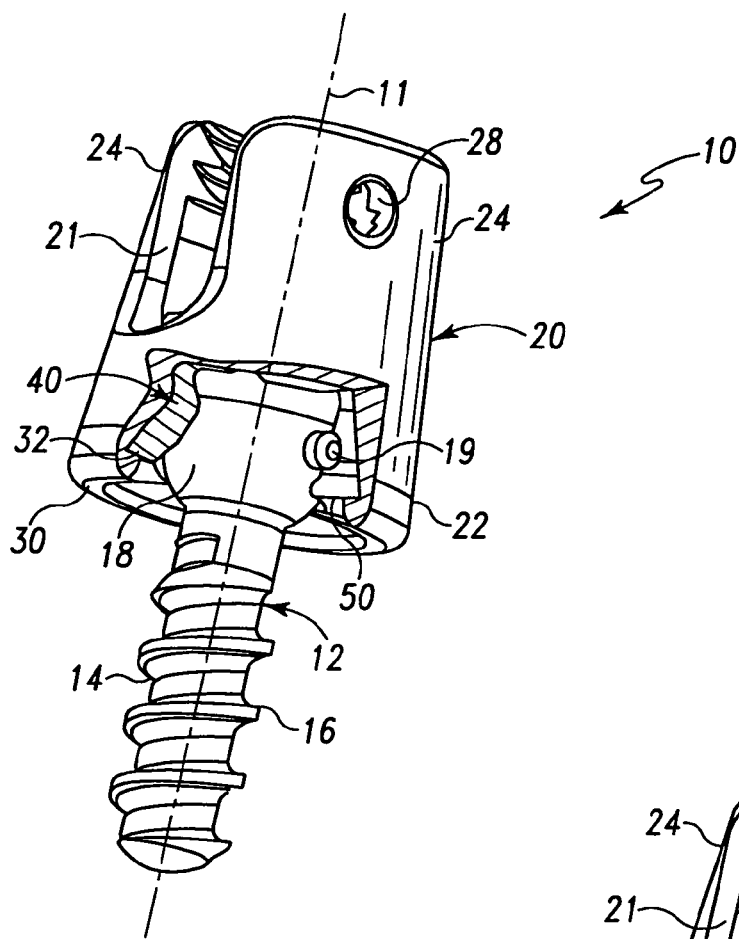
FIG. 2 is the anchor assembly of FIG. 1 in partial section.
Figure 3:
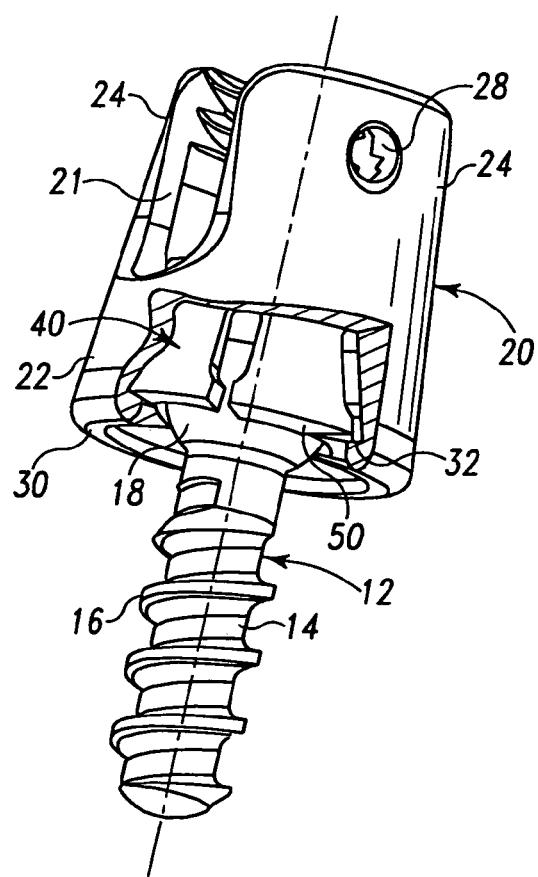
FIG. 3 is the anchor assembly of FIG. 1 assembled and in partial section.

Body 42 can also flex inwardly about these hinge portions 46 to allow the wall segments to radially compress and permit insertion of receiver member 20 over body 42. Pins 19 can travel to the proximal ends of passages 44, moving lip 56 about neck 15 of anchor member 12 and facilitating inward compression and deflection of the wall segments of body 42 about anchor member 12. When the distal end 30 of receiver member 20 is positioned distally past distal seat end 50, body 42 returns toward its non-compressed state in receiver member 20. Distal seat end 50 can abuttingly engage lip 32 about the distal end opening of receiver member 20, as shown in FIGS. 2 and 3. Head 18 and the pins 19 can move axially to the distal ends of proximal portions 44b of slots 44, but cannot pass through distal portions 44a since contact of body 42 with the inner surface of receiver member 20 thereabout prevents outward deflection of the wall segments of body 42. Head 18 is thus pivotally captured in retainer 40 with lip 56 of retainer 40 extending about a distally oriented surface of head 18.

Figure 5:
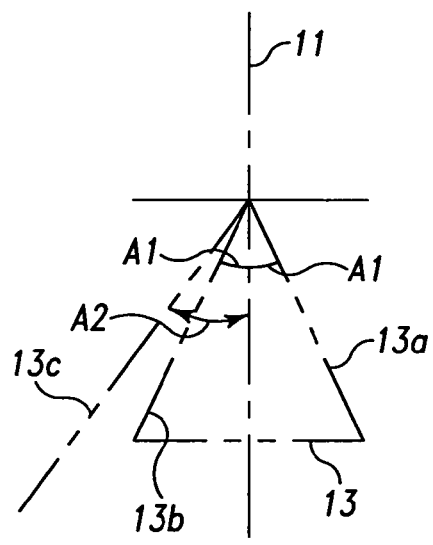
FIG. 5 is a diagram showing angular positions between the receiver member and the anchor member.

Distal seat end 50 further includes at least one cutout 54 forming a location about seat portion 50 to receive anchor member 12 in an increased angulation position relative to the angulation positions obtainable at the other locations about distal seat end 50. As shown in FIG. 5, receiver member 20 and anchor member 12 include a non-pivoted orientation where both are oriented along axis 11. Anchor member 12 and receiver member 20 are pivotal relative to one another so that the axis of anchor member 12 can be position along one of the pivot axes 13a, 13b, or along any axis between axes 13a, 13b. Anchor member 12 can also be configured to pivot about axis 11 in a conical pattern so that the relative positioning of the axes of anchor member 12 and receiver member 20 can lie anywhere in the conical space defined by pivot axes 13a, 13b. Cutout 54 is provided to provide a direction of increased angulation and allow greater adjustment capabilities between the axis of the anchor member and the axis of the receiver member. Accordingly, anchor member 12 can be pivoted in the location of cutout 54 to lie on axis 13c, which forms an angle A2 with axis 11 that is greater than angle A1 formed by the axes 13a, 13b.

Since hinge portions 46 are located adjacent the proximal end of body 42 and away from cutout 54, body 42 does not deform adjacent cutout 54 when retainer 40 is inserted into receiver member 20, or when anchor member 12 is inserted into retainer 40. Accordingly, the shape of cutout 54 is retained even after retainer insertion to allow anchor member 12 to be precisely and fully received in cutout 54. As shown in FIG. 5, cutout 54 receives neck 15 of anchor member 12 between head 18 and shaft 14 in the increased angulation position.

In use, anchor member 12 can be engaged to an underlying bony structure with retainer 40 loosely positioned about head 18. Alternatively, receiver member 20 can be assembled prior to engagement of anchor member 12 with bony structure. Receiver member 20 can be bottom-loaded onto anchor member 12 by positioning receiver member 20 about retainer 40 with retainer member 40 inwardly flexing as the distal end opening of receiver member 20 moves along the outer surface thereof. When the distal end opening of receiver member 20 is positioned distally of retainer 40, retainer 40 returns toward its initial configuration until retainer 40 contacts lip 32 about the distal end opening of receiver member 20, axially restraining anchor member 12 in receiver member 20.

The assembled anchor member and receiver member can then be engaged to bony structure, unless anchor member was engaged to the bony structure prior to assembly. If employed and if not already so positioned, seat member 70 can then be positioned through the proximal end opening of retainer 40 and into contact with head 18 of anchor member 12. Receiver member 20 can be manipulated into the desired alignment with implant 60.

Figure 4:
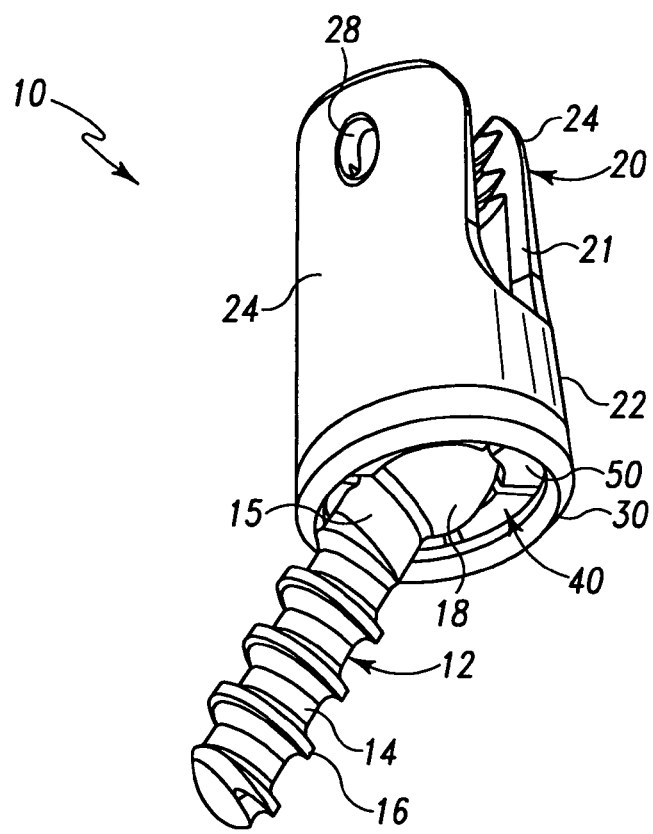
FIG. 4 is the anchor assembly of FIG. 1 assembled and pivoted to position the anchor in the increased angulation cutout of the retainer.

Anchor member 12 and receiver member 20 include a non-pivoted orientation shown in FIGS. 2-3 where each extends along a longitudinal axis 11. This orientation is shown graphically in FIG. 5. Anchor member 12 can be pivotal relative to receiver member 20 to any one of an infinite number of positions defining a cone 13 about axis 11. When anchor member 12 is aligned with cutout 54, as shown in FIG. 4, then the angular orientation of anchor member 12 relative to axis 11 is greater than at locations about retainer 40 not occupied by cutout 54. Accordingly, retainer 40 permits increased angulation of anchor member 12 relative to receiver member 20 to allow greater adjustment capabilities while maintaining sufficient structure about distal seat end 50 of retainer 40 to engage receiver member 20 and maintain anchor member 12 therein.

Cutout 54 can be aligned between arms 24 of receiver member 20 when it is desired to align pivot axis 13 along implant 60. Receiver member 20 can be pivoted to its maximum angular orientation relative to anchor member 12 so that anchor member 12 is located within cutout 54 to provide the desired alignment with implant 60. This can be desirable where the desired approach into the pedicle for anchor member 12 orients axis 11 in the cephalad or caudal direction. The increased angulation provided by retainer 40 can allow receiver member 20 to be pivoted so that passage 21 can be better aligned with the implant extending along the spinal column. Bending and manipulation of implant 60 to position it in receiver member 20 is minimized.

When the desired angular orientation between anchor member 12 and receiver member 20 is obtained, implant 60 is positioned between the arms of receiver member 20, and secured therein with engaging member 90. Engaging member 90 can be advanced into receiver member 20 into contact with implant 60, thereby pushing implant 60 into contact with seat member 70 and forcing seat member 70 into contact with head 18 of anchor member 12. In one embodiment, this positions seat member 70 into contact with head 18 of anchor member 12 to rigidly fix anchor member 12 in receiver member 20. Other embodiments contemplate that anchor member 12 maintains a variable angle or semi-rigid arrangement relative to receiver member 20 even when engaging member 90 and seat member 70 are firmly engaged to implant 60. Alternative arrangements are contemplated where implant 60 is forced into direct contact with anchor member 12 to lock it in position relative to receive member 20, or where anchor member 12 retains at least limited pivoting capabilities relative to receiver member 20 even when implant 60 is engaged to receiver member 20.

Implant 60 can be structured either alone or in combination with one or more other implants and/or coupling assemblies to provide a desired stabilization effect. In the illustrated embodiment, implant 60 is an elongated spinal rod structured to extend between at least two anchor assemblies 10, or between at least one anchor assembly 10 and another anchor, to stabilize a motion segment therebetween. Various forms for implant 60 are contemplated, including rods, tethers, cables, wires, plates, and staples, for example.

In spinal surgical procedures, implant 60 and one or more anchor assemblies 10 and other anchors discussed herein may be employed unilaterally. Alternatively, a second implant 60 and one or more anchor assemblies 10 and other anchors can be secured to the other side of the vertebral level or levels to be stabilized. Multiple implants 60 and corresponding anchor assemblies 10 and other anchors can be secured along the same side of the spinal column in either uni-lateral or bi-lateral stabilization procedures.

In one technique, the underlying bone forms a portion of a vertebral body of the spinal column. The underlying bone can be a part of the anterior, oblique, antero-lateral, lateral or posterior vertebral elements, including the pedicle, spinous process, transverse processes, lamina or facet, for example. Applications in techniques along any portion or portions of the spinal column are contemplated, including the cervical, thoracic, lumbar and sacral regions. The anchor assemblies and implants can be positioned along the spinal column in invasive procedures where skin and tissue are dissected and retracted to expose the implant locations, or in minimally invasive procedures where one or more the anchor assemblies and implants are guided through at least the tissue or access portals adjacent the column to the desired implantation location.

While the invention has been illustrated and described in detail in the drawings and foregoing description, the same is to be considered as illustrative and not restrictive in character. All changes and modifications that come within the spirit of the invention are desired to be protected.

What is claimed is:

1. A system for stabilizing a bony segment, comprising:
   an elongated implant;
   an anchor assembly engageable to said elongated implant to secure it to the spinal column, wherein said anchor assembly comprises:
      a receiver member defining a passage for receiving said implant and a distal opening extending transversely to said passage, said receiver further including a lip extending about said distal opening;
      an anchor member engageable to the bony segment, said anchor member including a head and a bone engaging portion extending through said distal opening;
      a seat member positioned between said implant and said anchor member; and
      a retainer including a distal seat end supported on said lip in said receiver member and a body defining a receptacle for pivotally receiving said head, said retainer extending proximally from said distal seat end and along said head of said anchor member to a proximal end, wherein said seat member is received in said receptacle and said retainer includes an outer wall surface that tapers proximally from said distal seat end to said proximal end when said retainer is supported on said lip in said receiver member;
      said head of said anchor member includes a pair of pins extending outwardly therefrom; and
      said retainer includes opposite passages extending in a wall thereof for rotatably receiving said pins therein; and
      wherein said head of said anchor member is pivotally engaged within said receptacle in said retainer when said pins are rotatably received and positioned within said opposite passages.

2. The system of claim 1, wherein said retainer further includes a retainer lip positionable in contact with a distal surface of said head and a cutout in said distal seat end of said body extending through said retainer lip and in communication with said receptacle, said cutout providing a location about said distal seat end of said retainer to receive said anchor member in a pivotal orientation relative to said retainer and said receiver member that provides a greater pivot angle than is attainable at locations about said retainer lip not occupied by said cutout.

3. The system of claim 1, wherein said pair of pins extending from said head of said anchor member each have a cylindrical configuration and are rotatably engaged with inner walls of said opposite passages in said retainer to thereby pivotally engage said head of said anchor member within said receptacle in said retainer.

4. The system of claim 1, wherein said pair of pins extending from said head of said anchor member each have a circular outer surface rotatably engaged with inner walls of said opposite passages in said retainer to thereby pivotally engage said head of said anchor member within said receptacle in said retainer.

5. The system of claim 1, wherein said opposite passages in said retainer extend through said wall from said outer wall surface to said receptacle.

6. The system of claim 1, wherein said outer wall surface of said retainer defines an inward taper extending proximally from said distal seat end to said proximal end.

7. The system of claim 1, wherein said retainer has a wall thickness that is lesser adjacent said proximal end than adjacent said distal seat end.

8. An anchor assembly for securing an elongated implant along the spinal column, comprising:
   a receiver member defining a passage for receiving the implant and a distal opening extending transversely to said passage;
   an anchor member engageable to the spinal column, said anchor member including a head and a bone engaging portion extending through said distal opening, said head including at least one pin extending outwardly therefrom; and
   a retainer in said receiver member including a body defining a receptacle pivotally capturing said head of said anchor member therein, said body including a proximal end and extends along said head to a distal seat end positionable in contact with said receiver member, said retainer including a number of axial passages in said body extending from said distal seat end to a location distal of said proximal end of said retainer, said number of passages each including a narrowed distal portion extending through said distal seat end of said retainer and a proximal portion extending from said narrowed portion to a living hinge at said proximal end of said retainer, wherein each of said proximal portions are wider than said distal narrowed portion from which said proximal portion extends with said number of passages dividing said body into a plurality of wall segments moveable relative to one another about said proximal end of said retainer body, wherein said at least one pin is received in one of said proximal portions and moves proximally and distally along said proximal portion as said retainer is moved relative to said head; and wherein said head of said anchor member is pivotally engaged within said receptacle in said retainer when said at least one pin is rotatably received and positioned within said proximal portion of a corresponding one of said axial passages.

9. The assembly of claim 8, wherein said at least one pin extending from said head of said anchor member has a cylindrical configuration and is rotatably engaged with opposite inner walls of said corresponding one of said axial passages in said retainer to thereby pivotally engage said head of said anchor member within said receptacle in said retainer.

10. The assembly of claim 8, wherein said at least one pin extending from said head of said anchor member has a circular outer surface rotatably engaged with opposite inner walls of said corresponding one of said axial passages in said retainer to thereby pivotally engage said head of said anchor member within said receptacle in said retainer.

11. The assembly of claim 8, wherein said head of said anchor member includes a pair of pins extending outwardly therefrom, said pair of pins rotatably received in proximal portions of an opposite pair of said axial passages to thereby pivotally engage said head of said anchor member within said receptacle in said retainer.

12. The assembly of claim 8, wherein said axial passages in said retainer each extend through a wall of said body from an outer wall surface of said body to said receptacle.

13. An anchor assembly for securing an elongated implant along the spinal column, comprising:

a receiver member defining a passage for receiving the implant and a distal opening extending transversely to said passage;

an anchor member engageable to the spinal column, said anchor member including a head and a bone engaging portion extending through said distal opening, said head including at least one pin extending outwardly therefrom; and a retainer in said receiver member including a body defining a receptacle pivotally capturing said head of said anchor member therein, said body including a proximal end and extends along said head to a distal seat end positionable in contact with said receiver member, said retainer including a number of axial passages in said body extending from said distal seat end to a location distal of said proximal end of said retainer, said number of passages each including a narrowed distal portion extending through said distal seat end of said retainer and a proximal portion extending from said narrowed portion to a living hinge at said proximal end of said retainer, wherein each of said proximal portions are wider than said distal narrowed portion from which said proximal portion extends with said number of passages dividing said body into a plurality of wall segments moveable relative to one another about said proximal end of said retainer body, wherein said at least one pin is received in one of said proximal portions and moves proximally and distally along said proximal portion as said retainer is moved relative to said head; and wherein said retainer further includes a lip positionable in contact with a distal surface of said head and a cutout in said distal seat end of said body extending through said lip and in communication with said receptacle, said cutout providing a location about said distal seat end of said retainer to receive said anchor member in a pivotal orientation relative to said retainer and said receiver member that provides a greater pivot angle than is attainable at locations about said lip of said retainer not occupied by said cutout.

14. An anchor assembly for securing an elongated implant along the spinal column, comprising:

a receiver member defining a passage for receiving the implant and a distal opening extending transversely to said passage;

an anchor member engageable to the spinal column, said anchor member including a head and a bone engaging portion extending through said distal opening, said head including at least one pin extending outwardly therefrom; and a retainer in said receiver member including a body defining a receptacle pivotally capturing said head of said anchor member therein, said body including a proximal end and extends along said head to a distal seat end positionable in contact with said receiver member, said retainer including a number of axial passages in said body extending from said distal seat end to a location distal of said proximal end of said retainer, said number of passages dividing said body into a plurality of wall segments moveable relative to one another about said proximal end of said retainer body, wherein said number of passages each includes a narrowed distal portion and a proximal portion, and at least one of said proximal portions rotatably receives said at least one pin extending from said head of said anchor member therein; and wherein said head of said anchor member is pivotally engaged within said receptacle in said retainer when said at least one pin is rotatably received and positioned within said proximal portion of a corresponding one of said axial passages.

15. The assembly of claim 14, wherein said pin is positionable into said receptacle of said retainer by contacting a respective one of said narrowed distal portions with said pin and flexing adjacent wall segments outwardly to permit passage of said pin through said distal narrowed portion to said proximal portion of said passage.

16. The assembly of claim 14, wherein said retainer further includes a retainer lip positionable in contact with a distal surface of said head and a cutout in said distal seat end of said body extending through said retainer lip and in communication with said receptacle, said cutout providing a location about said distal seat end of said retainer to receive said anchor member in a pivotal orientation relative to said retainer and said receiver member that provides a greater pivot angle than is attainable at locations about said retainer lip not occupied by said cutout.

17. The assembly of claim 14, wherein said at least one pin extending from said head of said anchor member has a cylindrical configuration and is rotatably engaged with opposite inner walls of said corresponding one of said axial passages in said retainer to thereby pivotally engage said head of said anchor member within said receptacle in said retainer.

18. The assembly of claim 14, wherein said at least one pin extending from said head of said anchor member has a circular outer surface rotatably engaged with opposite inner walls of said corresponding one of said axial passages in said retainer to thereby pivotally engage said head of said anchor member within said receptacle in said retainer.

19. The assembly of claim 14, wherein said head of said anchor member includes a pair of pins extending outwardly therefrom, said pair of pins rotatably received in proximal portions of an opposite pair of said axial passages to thereby pivotally engage said head of said anchor member within said receptacle in said retainer.

20. The assembly of claim 14, wherein said axial passages in said retainer each extend through a wall of said body from an outer wall surface of said body to said receptacle.

* * * * *